April 19, 1938.
J. H. KLUIS
HYDRANGEA
Filed Aug. 2, 1937
Plant Pat. 276
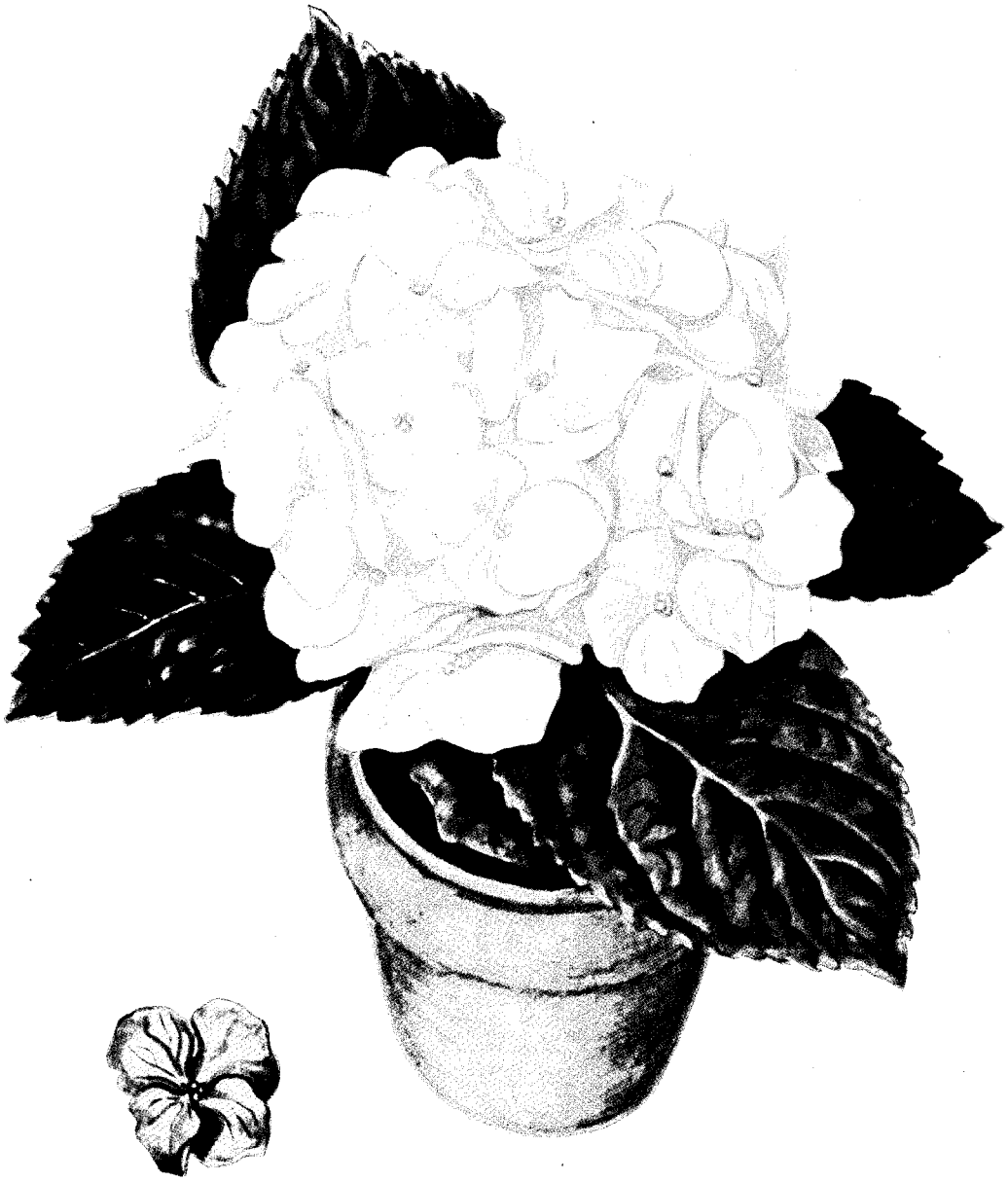
INVENTOR
John H. Kluis
By Orville M. Kile
PLANT PATENT AGENT Patented Apr. 19, 1938

Plant Pat. 276

UNITED STATES PATENT OFFICE

276

HYDRANGEA

John H. Kluis, Boskoop, Netherlands, assignor to Joseph S. Merritt, Dundalk, Md.

Application August 2, 1937, Serial No. 157,029

1 Claim. (Cl. 47—60)

My present invention relates to improvements in the type of hydrangeas particularly adapted to greenhouse forcing. This variety was obtained by crossing the varieties M. Foch and La Marne. The cross has apparently resulted in a plant having the good qualities of both parents and without the bad habits of either. Propagation by means of soft wood cuttings has been carried on through several generations and the qualities and characteristics of the new variety appear to be permanent.

The object of my invention is to provide a new and distinct variety of pink hydrangea, having the following desirable characteristics; freedom of flowering and of setting buds, compactness of flower trusses, earliness of blooming, ease with which color can be changed by acid application to soil, production of flowers and leaves of heavy substance, and adaptability to forcing for early blooming. Such a plant is particularly desirable in forcing flowers for an early Easter.

The original illustration accompanying this application shows a complete young forced plant in its original color, together with an individual blossom or ray flower of a plant which has been treated with an acid solution at its roots, showing one of the blue shades thus obtainable. References to color plates indicate Ridgway's Color Standards and Nomenclature, issue of 1912.

Following is a more complete description of the plant and flower.

*The plant*

*Growth habits.*—Under ordinary outdoor conditions this variety grows very large with exceedingly compact and large blossom heads. As a forced greenhouse plant they will bloom when only a few inches high. In fact, some perfect forced specimens are about six inches high—one-half of which is the bloom. Free growing. More vigorous grower than either parent. In a favorable outdoor location it grows to a height of from two to three feet being a bit taller than its parent, M. Foch.

*Blooming habits.*—Produces compact, globose flower truss. Free blooming. Sets buds freely and as early as M. Foch.

*Foliage.*—Glossy; heavier than most varieties.

*Leaves.*—Appear in pairs directly opposite. In the small, forced plant several pairs, with varying lengths of stems, arrange themselves at right angles around the globular flower cluster thus forming a background of green leaves framing the flower cluster.

*Color.*—Cress Green to Yew Green (Plate XXXI) with gloss. Under side, Light Cress Green (Plate XXXI).

*Shape.*—Ovate; margin deeply and sharply serrate.

*Size.*—In the forced plant six inches high the leaves are from four to five inches long and two and three-fourths to three and one-fourth inches wide. In the larger outdoor plants the leaves are proportionately larger.

*Appearance.*—Glossy, heavy substance, veining very prominent, principal veins parallel from midrib to margin.

*Stems.*—Erect and stiff; same color as under side of leaf.

*Peduncle.*—Lengths vary according to position on stem; stiff; grooved on upper side.

*The flower*

*Blossom.*—Large, compact, globose flower truss, sometimes attaining a spread of eight to ten inches.

*Individual florets.*—Composed of four petals opening flat but overlapping, together with a center consisting of a compound pistil surrounded by eight stamens of unequal lengths. When flower first opens, stamens are inclosed within four rudimentary scales or caps which in most instances drop off very early.

*Color.*—Geranium Pink (Plate I). By addition of acid to soil, flowers of blue color can be produced the predominating shade being corn flower blue (Plate XXI).

*Stamens.*—Uneven filaments. Anthers divided into two lobes, and are large compared to size of filaments.

*Petals.*—Flattened, orbicular, with obcordate tip. Veinings prominent. Substance heavy.

*Fertility.*—All florets are fertile under average growing conditions.

Having thus disclosed my invention, I claim as new:

The variety of hydrangea herein described and illustrated, characterized particularly by its earliness of blooms, freedom of production of large, compact flower trusses of heavy substance and deep pink color as shown and described, the ease with which color of blossoms can be changed to blue by acid application to roots; and the foliage of unusually heavy substance and quantity.

JOHN H. KLUIS.